United States Patent [19]

Hayashi

[11] Patent Number: 5,268,735
[45] Date of Patent: Dec. 7, 1993

[54] APPARATUS FOR OBSERVING FEATURES AND DEFECTS OF A SAMPLE

[75] Inventor: Ryutaro Hayashi, Tokyo, Japan

[73] Assignee: International Business Machines Corporation, Armonk, N.Y.

[21] Appl. No.: 802,975

[22] Filed: Dec. 6, 1991

[30] Foreign Application Priority Data

Dec. 14, 1990 [JP] Japan ................................. 2-410532

[51] Int. Cl.$^5$ ............................................. G01N 21/00
[52] U.S. Cl. ..................... 356/237; 356/430; 356/239; 250/562; 358/106
[58] Field of Search .................. 356/237, 239, 394, 73, 356/429, 430, 445; 250/562, 572, 563, 571; 382/8; 364/507; 358/101, 106, 107

[56] References Cited

U.S. PATENT DOCUMENTS

| | | | |
|---|---|---|---|
| 3,972,616 | 8/1976 | Minami et al. | 356/239 |
| 4,647,208 | 3/1987 | Bieman | 356/394 |
| 4,648,053 | 3/1987 | Fridge | 356/394 |
| 4,737,649 | 4/1988 | Naruse | 250/562 |
| 4,958,083 | 9/1990 | Sakamoto | 250/572 |
| 5,031,112 | 7/1991 | Sakai et al. | 356/237 |
| 5,098,191 | 3/1992 | Noguchi et al. | 356/237 |

FOREIGN PATENT DOCUMENTS 61-25041 6/1986 Japan .

Primary Examiner—Richard A. Rosenberger
Assistant Examiner—Hoa Q. Pham
Attorney, Agent, or Firm—D. A. Shifrin

[57] ABSTRACT

According to the present invention, an optical inspection apparatus which can observe a light-transmitted portion and a light-reflected portion within objects of inspection, distinguishable from each other within the same field of vision, is provided.

4 Claims, 2 Drawing Sheets

APPARATUS FOR OBSERVING FEATURES AND DEFECTS OF A SAMPLE

FIELD OF THE INVENTION

The present invention relates to an optical inspection apparatus, and more particularly to an optical inspection apparatus for observing a light-transmitted portion and a light-reflected portion of a sample to be inspected within the same visual field.

BACKGROUND OF THE INVENTION

The main defects which are caused in an optical disk are pin holes in a recording layer and foreign substances absorbed on the surface of the recording layer or mixed in a transparent substrate. To inspect the above defects, a prior art solution has used an optical microscope constructed so that an image is caused by light reflected from the optical disk.

Accordingly, as shown in FIG. 3, pin holes 11 and foreign substances 12 on an optical disk 1 are observed as black shadows (points). Thus the pin holes 11 and the foreign substances 12 have been indistinguishable from one another. Further, in a case where the optical disk 1 is inspected by an optical microscope constructed so that an image is caused by light transmitted through the optical disk 1, even though the pin holes 11 can be observed, it is very difficult to observe the foreign substances 12 because the recording layer, being made of metal, has a low transmittance of light. Still further, coaxial or spiral grooves 2 formed on the optical disk 1 can be observed from the reflected light image, but it is difficult to observe the grooves 2 from the transmitted light image. For this reason, the grooves 2 and the pin holes 11 cannot be observed at the same time with the optical microscope constructed so that the transmitted light image from the optical disk 1 is observed and thus it is impossible to find out the law of causation from investigating the relationship of the grooves 2 with the pin holes 11.

Japanese Published Unexamined Patent Application (PUPA) 61-25041 discloses a bottle inspection apparatus in which the neck and the bottom portions of a bottle are observed by reflected light and transmitted light, respectively. However, in the bottle inspection apparatus, a portion where a reflected light image is caused and a portion where a transmitted light image is caused, are previously separated from each other within a visual field of inspection. Therefore, the bottle inspection apparatus cannot be applied to a usual object to be inspected, as in an inspection of the optical disk, in which a portion (pin hole) through which light transmits and a portion (foreign substance) from which light reflects are mixed.

SUMMARY OF THE INVENTION

An object of the present invention is to provide an optical inspection apparatus in which a light-transmitted portion and a light-reflected portion within a sample to be inspected, distinguishable from each other can be observed within the same field of vision.

According to the present invention, the transmitted light image and the reflected light image of a sample to be inspected are formed by one and the other of at least two lights, respectively, distinguishable from each other to accomplish said object of the present invention.

The foregoing and other objects, features and advantages of the invention will be apparent from the following more particular description of the preferred embodiment of the invention, as illustrated in the accompanying drawing.

DETAILED DESCRIPTION

Figure 1:
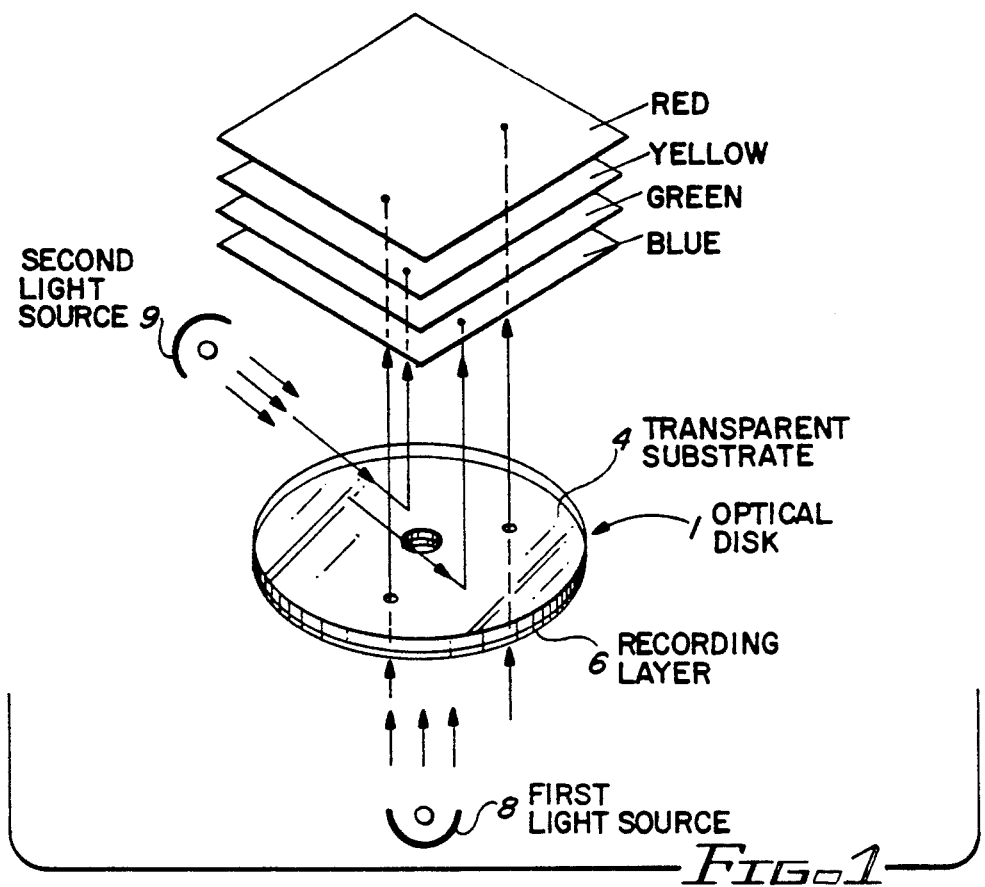
FIG. 1 is a perspective view showing a basic concept of the embodiment of an optical inspection apparatus according to the present invention.

In the following, an embodiment of the present invention is described by reference to the drawing. FIG. 1 shows a concept of the embodiment of an optical inspection apparatus constructed in accordance with the present invention. Referring to the figure, an optical disk 1 to be inspected comprises a transparent substrate 4 and a recording layer 6. Foreign substances 12 are mixed in the substrate 4 and attached to the recording layer 6 and pin holes 11 are made in the recording layer 6.

Light from a first light source 8 is irradiated onto one side of the optical disk 1 and light from a second light source 9 is irradiated onto the other side of the optical disk 1. The first light source 8 is arranged so that the light irradiated from the light source 8 transmits through the optical disk 1 to form an image. The second light source 9 is arranged so that the light irradiated from the light source 9 is reflected from the optical disk 1 to form another image. The intensity of the light irradiated from the first light source 8 is higher than that of the light irradiated from the second light source 9.

The light from the first light source 8 transmits through the pin holes 11 (shown in FIG. 2) which penetrate the recording layer 6 to form the images of the pin holes 11. The light from the second light source 9 is reflected from the recording layer 6 and grooves 2 (shown in FIG. 2) to form the images of the recording layer 6 and the grooves 2. Also, the light from the second light source 9 is reflected from foreign substance 12 (shown in FIG. 2) to form the images of the foreign substances 12. As comparing brightnesses in these images, it is obvious that the images of the pin holes 11 are brightest, the images of flat portions on the recording layer 6 are second to those of the pin holes 11, and the images of the grooves 2 around which the light is scattered are darker than those of said flat portions. Because light is absorbed or scattered if it is reflected from the foreign substances 12, the images of the foreign substances 12 become still darker than the images of the recording layer 6 and the grooves 2.

FIG. 1 shows that the images thus formed, of respective portions are converted into colors different from one another in accordance with their brightnesses. For example, the brightest images of the pin holes 11, the images of the flat portions on the recording layer 6, the images of the grooves 2, and the images of the foreign substances 12 are converted into red, yellow, green and blue colors respectively.

Figure 4:
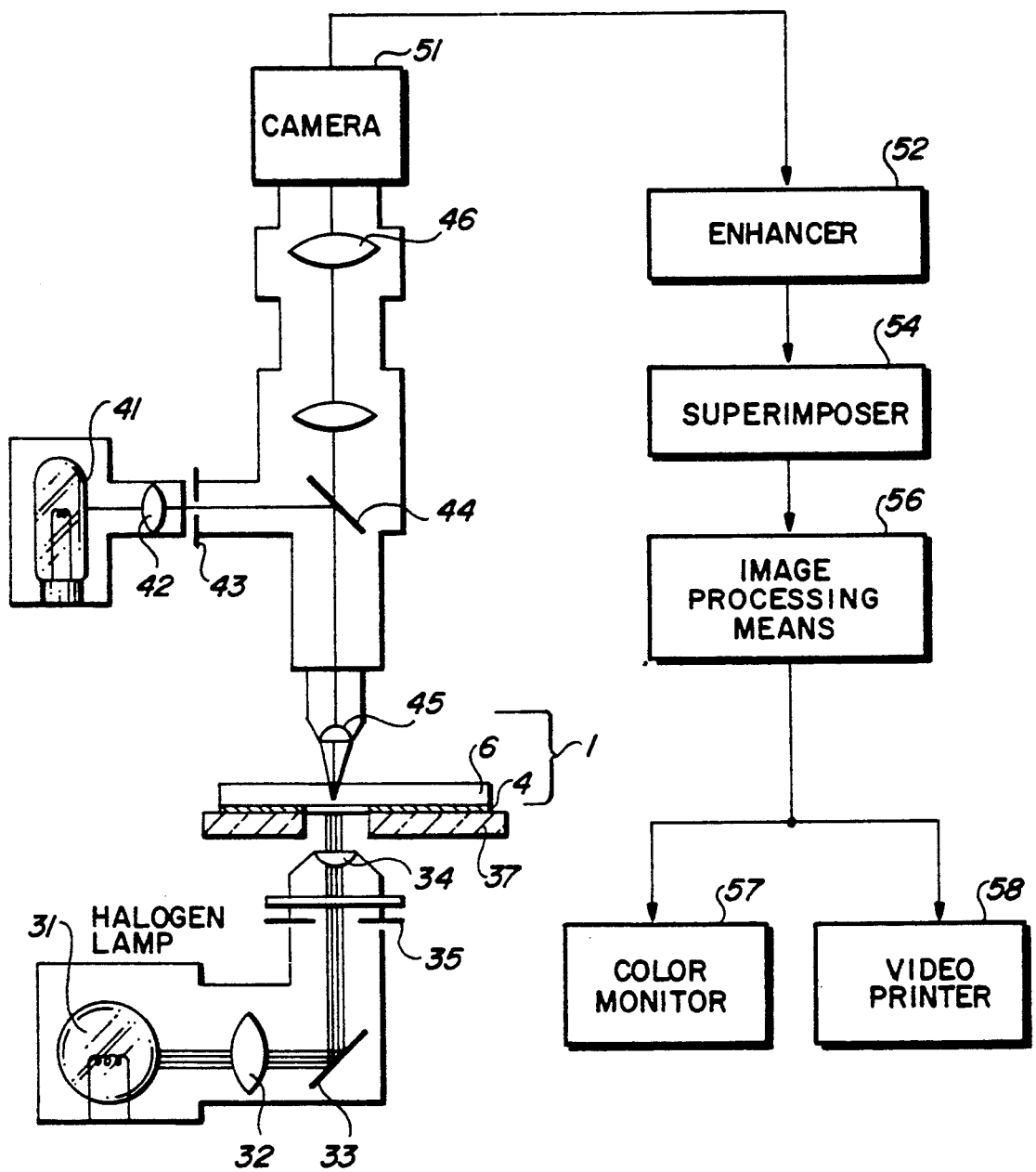
FIG. 4 is a cross-sectional view showing the preferred embodiment of FIG. 1 in greater detail.

FIG. 4 shows in detail the optical disk of said embodiment. In the figure, the light from a first halogen lamp 31, which is the first light source, is irradiated, via a collimator lens 32, a mirror 33, an aperture 35, and then a beam condenser 34, onto the bottom of the optical disk 1 on a transparent sample base 37. The light from a second halogen lamp 41, which is the second light source, is irradiated, via a collimator lens 42, an aperture 43, and a half mirror 44, onto the topside of the optical disk 1. The first halogen lamp 31 is, for example, twice as bright as the second halogen lamp 41.

The transmitted light and the reflected light from the optical disk 1 pass through a relay lens 46, fall on a photo sensitive material of a camera 51, which is a photo detective means, and then are converted into picture image signals. The camera 51 is a monochrome camera, for example, a CCD (charge coupled device) camera. The resolving power of the monochrome camera 51 is superior to that of a color camera. The picture image signals from said camera 51 are provided, via an image enhancer 52 and a superimposer 54, to image processing means 56. The image enhancer 52 processes the picture image signals to highlight the outlines of the images, while the superimposer 54 adds gauge information, sample name information, etc. to a part of the visual field. The image processing means 56 performs integrating processing for reducing noise and then coloring processing for each portion of the images in accordance with the quantity of light, that is, the image processing means 56 generates picture image signals for presenting the images in colors different from one another in accordance with the intensity of light.

Figure 2:
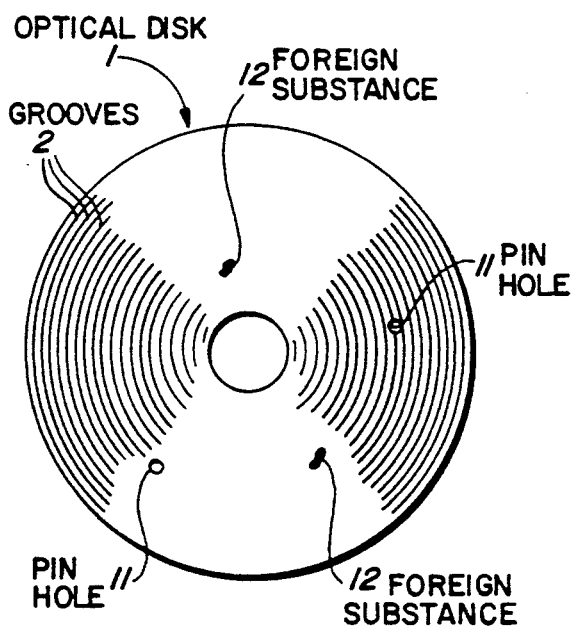
FIG. 2 is a plan view showing a result of inspection of the optical disk according to said embodiment.
Figure 3:
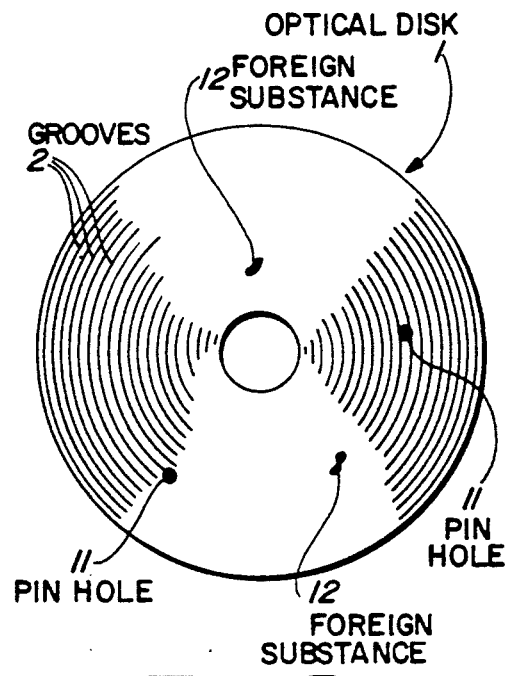
FIG. 3 is a plan view showing a result of inspection of an optical disk with a conventional optical microscope.

To the image processing means 56, a color monitor 57 and a video printer 58, which are presentation means, are attached. The color monitor 57 displays the images in colors different from one another on the screen based on the picture image signals from said image processing means 56, while the video printer 58 prints the images in colors different from one another based on the picture image signals from said image processing means 56. FIG. 2 shows a result of display on the screen of the color monitor 57 or printing to the video printer 58. If FIG. 2 was in color, the pin holes 11, foreign substances 12, and the grooves 2 would be shown in colors different from one another.

According to the embodiment, a clear distinction of whether observed defects are caused by the pin holes 11 made in the recording layer 6, or the foreign substances 12 attached to the recording layer 6 or mixed in the substrate 4 can be drawn. Therefore, useful information for investigating that the defects have been caused at any stage in the manufacturing process of the optical disk 1 can be obtained. Further, by printing results obtained from several life tests for the optical disk 1 in colors to the video printer 58 and overlapping them on each other, the presence or absence, and the degree, of the growth of defects according to the types of the defects can be investigated. Further, since a color of each portion of the images corresponds with each type of the defects, in such a manner that, for example, even if a defect has been observed in yellow a decision that shipment is possible can be made, or if a defect has been observed in red a decision that shipment is impossible can be made. Hence products can be inspected efficiently based on colors observed. Still further, since the grooves 2 and the pin holes 11 can be observed within the same field of vision, useful information for investigating the effects of the grooves 2 on the pin holes 11 can be obtained. And furthermore, since the embodiment is constructed so that a monochrome camera, which can obtain easily higher resolving power than a color camera, is used, even a minute defect can be inspected easily.

While the invention has been particularly described with reference to particular embodiments thereof, it will be understood by those skilled in the art that various other changes in detail may be made therein without departing from the spirit, scope, and teaching of the invention. In the embodiment, although light which causes a transmitted light image and light which causes a reflected light image differ from each other in brightness (quantity of light), both were able to distinguish from each other in different colors after the picture image processing. However, it will be appreciated that light for the transmitted light image and light for the reflected light image which differ in wavelengths (colors) may be used so that both can be distinguished from each other without the need of the picture image processing. It will appreciated also that other distinguishable optical characteristics may be used, for example, a transmitted light image may be formed by one of different polarized lights and a reflected light image may be formed by the other and then the images may be distinguished from each other in colors based on the types of polarized lights. It will be appreciated also that the present invention can be applied not only to the inspection of the optical disk, but also to the inspection of others than the optical disk which can form images by transmitted light and reflected light.

Accordingly, the invention herein disclosed is to be limited only as specified in the following claims.

What is claimed is:

1. An optical inspection apparatus for generating a picture image of an optical disk, wherein a first defect type is distinguishable from a second defect type in the image, the apparatus comprising:
    a first light source, having a first intensity, for irradiating a first side of a recording layer of the optical disk and reflecting light therefrom whereby features and defects of the first side are detachable;
    a second light source, having a second intensity different from the first intensity, for irradiating a second side of the recording layer and transmitting light through defects extending through the recording layer;
    a black and white video camera facing the first side for receiving the reflected light and the transmitted light in the same field of vision;
    image processing means, responsive to said black and white video camera, for generating a composite picture image signal; and
    a color monitor coupled for receiving the composite picture image signal from said image processing means and displaying the defects of the first side in a first color, the defects extending through the recording layer in a second color and the features of the first side in at least a third color.

2. The optical inspection apparatus according to claim 1 wherein the first light source is a halogen lamp.

3. The optical inspection apparatus according to claim 1 wherein the second light source is a halogen lamp.

4. The optical inspection apparatus according to claim 1 wherein the optical disk includes a transparent substrate overlaying the first side of the recording layer and light from the second light source passes through the transparent substrate, said color monitor further comprising means for displaying defects within the transparent substrate in a fourth color.

* * * * *

UNITED STATES PATENT AND TRADEMARK OFFICE
CERTIFICATE OF CORRECTION

PATENT NO. : 5,268,735
DATED : December 7, 1993
INVENTOR(S) : Ryutaro Hayashi

It is certified that error appears in the above-identified patent and that said Letters Patent is hereby corrected as shown below:

At column 4, line 39, the word "detachable" should be --detectable--.

Signed and Sealed this

Tenth Day of May, 1994

Attest:

BRUCE LEHMAN

Attesting Officer          Commissioner of Patents and Trademarks